US00PP34639P2

(12) United States Plant Patent
Roberts et al.

(10) Patent No.: US PP34,639 P2
(45) Date of Patent: Oct. 11, 2022

(54) ***LAGERSTROEMIA* PLANT NAMED 'BAILLAGTWO'**

(50) Latin Name: ***Lagerstroemia* hybrid**
Varietal Denomination: Baillagtwo

(71) Applicant: Bailey Nurseries, Inc, Newport, MN (US)

(72) Inventors: David Jonathan Roberts, Athens, GA (US); Oren McBee, Bishop, GA (US); Justin Schulze, Bishop, GA (US)

(73) Assignee: BAILEY NURSERIES INC., Newport, MN (US)

( * ) Notice: Subject to any disclaimer, the term of this patent is extended or adjusted under 35 U.S.C. 154(b) by 0 days.

(21) Appl. No.: 17/578,541

(22) Filed: Jan. 19, 2022

(51) Int. Cl.
*A01H 5/02* (2018.01)
*A01H 6/00* (2018.01)

(52) U.S. Cl.
USPC ..... Plt./252

(58) Field of Classification Search
USPC ..... Plt./252
CPC ... A01H 5/02; A01H 5/00; A01H 5/04; A01H 6/00; A01H 1/107
See application file for complete search history.

*Primary Examiner* — June Hwu
(74) *Attorney, Agent, or Firm* — Penny J. Aguirre

(57) ABSTRACT

A new cultivar of *Lagerstroemia* plant named 'Baillagtwo' that is characterized by its leaves that are held primarily flat in aspect, its glossy foliage that is dark purple in color, its flowers that are dark pink in color, its rounded and upright plant habit, and its resistance to powdery mildew.

2 Drawing Sheets

Botanical classification: *Lagerstroemia* hybrid.
Variety denomination: 'Baillagtwo'.

BACKGROUND OF THE INVENTION

The present invention relates to a new and distinct cultivar of *Lagerstroemia* of hybrid origin. The new *Lagerstroemia* will hereafter be referred to by its cultivar name, 'Baillagtwo'. 'Baillagtwo' is a new cultivar of crape myrtle grown for use as an ornamental landscape plant.

The new cultivar was derived from a controlled breeding program conducted by the Inventors in Watkinsville, Ga. The objective of the breeding program is to develop a new cultivars of crape myrtle with compact plant habits, disease resistance combined with unique foliage and flower characteristics.

'Baillagtwo' originated as a seedling that arose from seed planted from open pollination of an unnamed and unpatented plant of *Lagerstroemia* from the Inventors' breeding program; reference no. LAG16-03-09, in summer of 2016. The male parent is therefore unknown. 'Baillagtwo' was selected as a single unique plant in summer of 2018 from the resulting seedlings.

Asexual propagation of the new cultivar was first accomplished by softwood stem cuttings by one of the Inventors in Winterville, Ga. in summer of 2018. Asexual propagation by softwood stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Baillagtwo' as a unique cultivar of *Lagerstroemia*.

1. 'Baillagtwo' exhibits leaves that are held primarily flat in aspect.
2. 'Baillagtwo' exhibits glossy foliage that is dark purple in color.
3. 'Baillagtwo' exhibits flowers that are dark pink in color.
4. 'Baillagtwo' exhibits a rounded and upright plant habit.
5. 'Baillagtwo' exhibits resistance to powdery mildew.

The female parent of 'Baillagtwo' differs from 'Baillagtwo' in having foliage that is curled upward, lighter in color, and less glossy and flowers that are lighter pink in color. 'Baillagtwo' can also be compared to the *Lagerstroemia* cultivars 'PIILAG-V' (U.S. Plant Pat. No. 25,925) and '1LI' (U.S. Plant Pat. No. 28,065). 'PIILAG-V' and '1LI' are both similar to 'Baillagtwo' in having purple foliage and pink flowers. 'PIILAG-V' differs from 'Baillagtwo' in having foliage that is curled, lighter in color, and less glossy, flowers that are lighter pink in color, and a less rounded plant habit. '1LI' differs from 'Baillagtwo' in having foliage that is curled upward, lighter in color, and less glossy, and flowers that are lighter pink in color.

BRIEF DESCRIPTION OF THE DRAWINGS

The accompanying color photographs illustrate the overall appearance and distinct characteristics of the new.

The photograph on FIG. 1 was taken of a 3-year-old plant of 'Baillagtwo' as grown in a trial garden in Winterville, Ga. and provides a side view of 'Baillagtwo' in bloom.

Figure 1:
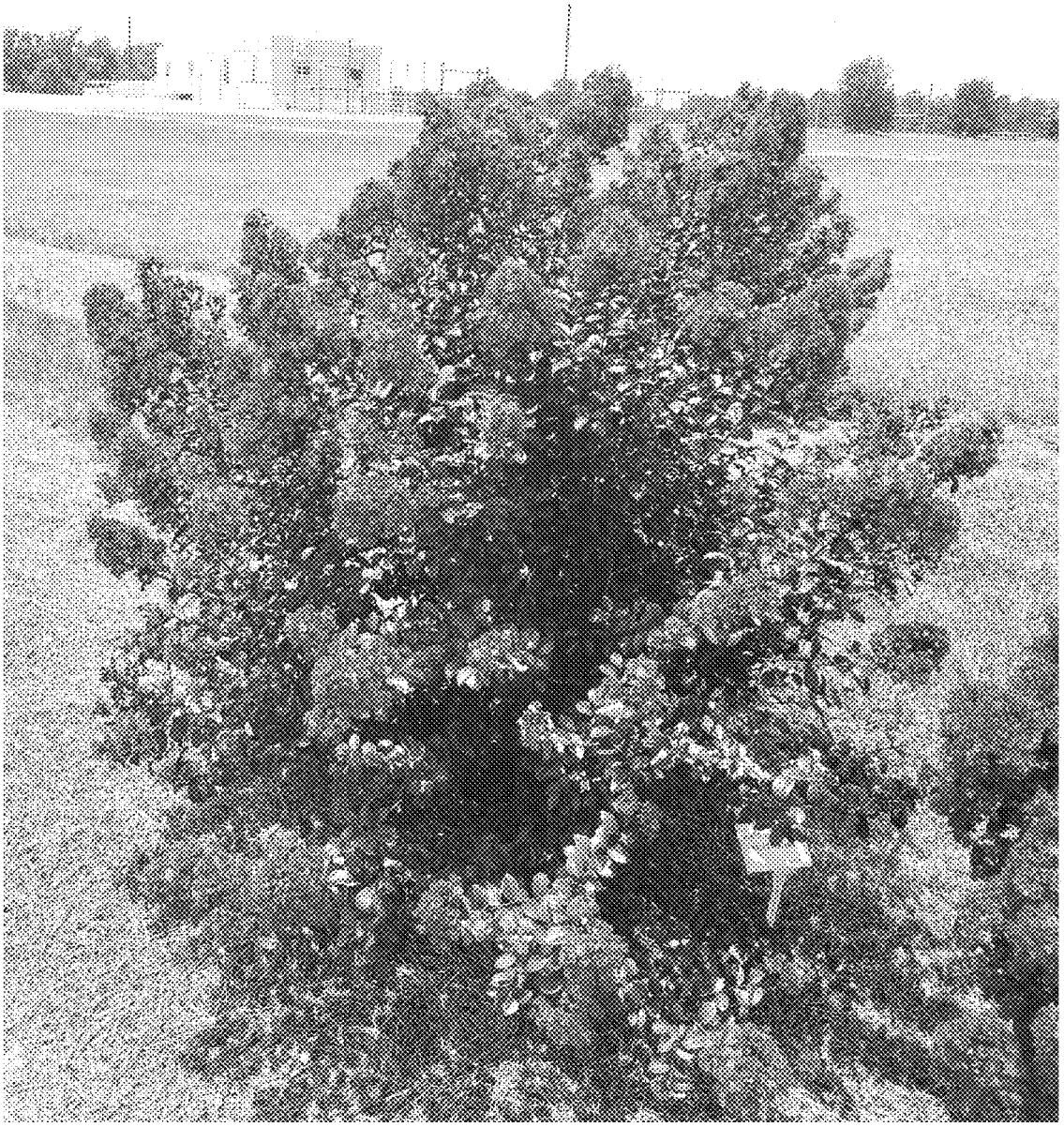
Figure 2:
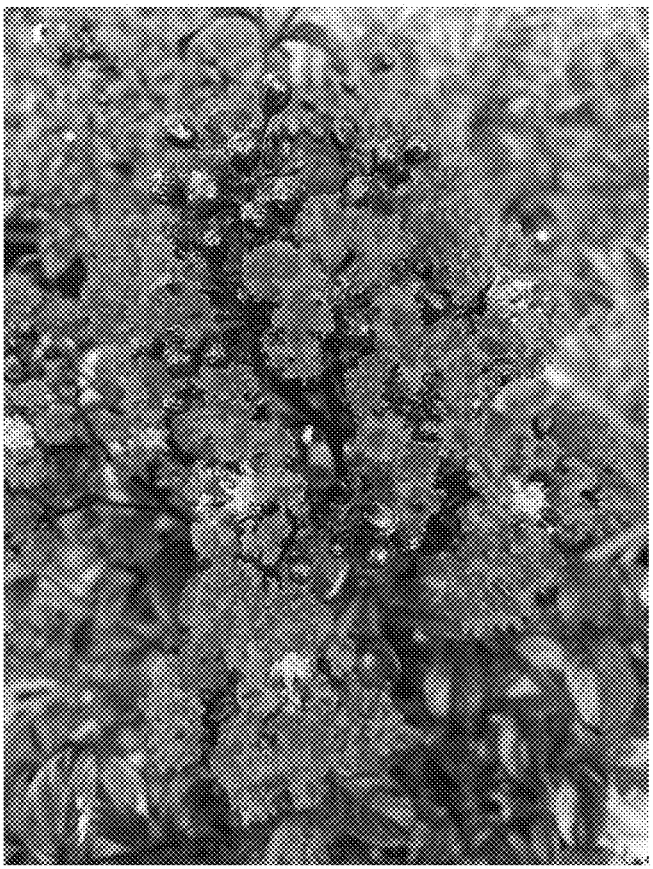
Figure 3:
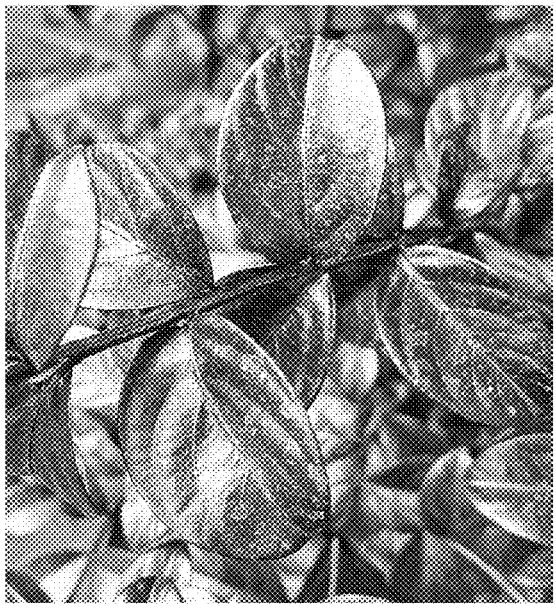

The photographs in FIG. 2 and FIG. 3 were taken of a 1.5-year-old plant of 'Baillagtwo' as grown outdoors in a 2-gallon container in Newport, Minn. The photograph in FIG. 2 provides a close-up view of the flowers of 'Baillagtwo'. The photograph in FIG. 3 provides a close-up view of the foliage of 'Baillagtwo'.

The colors in the photographs are as close as possible with the photographic and printing technology utilized and the color values cited in the Detailed Botanical Description accurately describe the colors of the new *Lagerstroemia*.

DETAILED BOTANICAL DESCRIPTION

The following is a detailed description of a 1.5-year-old plants of the new cultivar as grown in a greenhouse followed by outdoors in 2-gallon containers in full sun in Cottage Grove, Minn. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Mid-July in Winterville, Georgia, lasting 4 to 6 weeks.

*Plant type*.—Deciduous flowering shrub.

*Plant habit*.—Compact and upright of intermediate stature, finely textured and dense, freely branched without pruning.

*Height and spread*.—An average of 97 cm in height and 82 cm in width as grown in a 2-gallon container and an average of 2.7 m in height and 2.1 m in width as a mature plant in the landscape.

*Hardiness*.—At least in U.S.D.A. Zones 7 to 9.

*Diseases and pests*.—Has shown resistant to powdery mildew (caused by *Erysiphe lagerstroemiae*), no resistance or susceptibility to pests has been observed.

*Root description*.—155A in color, young roots are fibrous and fine.

*Root development*.—An average of 6 weeks at 32° C. for root initiation and an average of 3 months at 32° C. to produce a young rooted plant.

*Propagation*.—Semi-hardwood stem cuttings.

*Growth rate*.—Moderately vigorous.

Branch description:

*Branch shape*.—Quadrangular on young stems, oval on mature stems, round trunk.

*Branch color*.—Young stems; not in sun 187A in color, when in sun the edges are vibrant and 185A, center 187A, mature stems; 200A, turning 198A as the branches age, surface under exfoliating bark N170A, old bark; N200A with streaks of 200D.

*Branch size*.—Main branches; 35 cm in length, 1 cm in diameter, lateral branches; 21 cm in length, 3 mm in diameter, trunk; multi-branched and 1.5 cm in diameter at soil level.

*Branch surface*.—Young stems; glabrous and very glossy.

*Branch strength*.—Young; flexible and strong, mature; strong.

*Branching*.—Freely branching habit (without pruning), main branches; 3, lateral branches per main branch; 15.

*Branch aspect*.—Held upright at angles ranging between 45° to 75°.

*Internode length*.—An average of 3 cm.

Foliage description:

*Leaf shape*.—Elliptic.

*Leaf division*.—Single.

*Leaf base*.—Cuneate.

*Leaf apex*.—Acuminate.

*Leaf venation*.—Pinnate, upper surface; inconspicuous, lower surface 184A.

*Leaf margins*.—Entire.

*Leaf arrangement*.—Sub-opposite to alternate.

*Leaf attachment*.—Sessile.

*Leaf surface*.—Both surfaces glabrous and glossy.

*Leaf size*.—An average of 4.5 cm in length and 2 cm in width.

*Leaf quantity*.—An average of 34 per lateral branch.

*Leaf color*.—Emerging leaves upper and lower surface; 187A and 187B, young and mature upper surface; 202A with slight tones of 187A, young and mature lower surface; 200A and 185A if lower surface is exposed to sun.

Flower description:

*Inflorescence type*.—Terminal panicle.

*Lastingness of inflorescence*.—Inflorescences last for 4 to 6 weeks, individual flowers last an average of 1 day, self cleaning.

*Inflorescence size*.—An average of 22 cm in height and 17 cm in width.

*Inflorescence number*.—One per lateral branch.

*Flower number*.—An average of 50 to 150 flowers and flower buds per inflorescence.

*Flower fragrance*.—Faintly sweet scent.

*Flower buds*.—Globose in shape, an average of 9 mm in length, 6 mm in depth, pointed apex, surface is glabrous and very glossy with six distinct lines at petal margins, color; 183A, margin lines 202A.

*Flower aspect*.—Upright to outward.

*Flower type*.—Rotate.

*Flower size*.—An average of 1.5 cm in height and 4 cm in diameter.

*Petals*.—Typically 7, rotate in arrangement, fan-shaped, curling downward, heavily ruffled margins, sagittate base with a long thin attachment 6 mm in length, 0.5 mm in width, ruffled and rounded apex, both surfaces glabrous, satiny, an average of 1.5 cm in length and 1.2 in width, color; when bursting from bud upper and lower surface 73B, margins 75D, when fully open upper and lower surface a blend of 60A and 60B.

*Calyx*.—Consists of 6 fused sepals, acute apices, an average of 4 mm in length and 3 mm in diameter, smooth, glabrous on both surfaces, outer surface very glossy, color; outer surface a blend of 187A and slightly flushed with 187B, inner surface 192A.

*Peduncles*.—Strong, quadrangular, edges of angles slightly wavy, an average of 4.5 cm in length and 3 mm in diameter, surface is glabrous and very glossy, not in sun 187A in color, when in sun the edges are vibrant and 185A, center 187A.

*Pedicels*.—Strong, quadrangular, edges of angles slightly wavy, an average of 8 mm in length and 1 mm in diameter, surface is very glossy and slightly covered in very short minute hairs 0.2 in length, NN155D in color, color; not in sun 187A in color, when in sun the edges are vibrant and 185A, center 187A.

Reproductive organs:

*Stamens*.—25 to 30 shorter curled stamens, clustered more in the center, 9 mm in length surrounded by 4 longer stamens, 1.3 cm in length, glabrous surface, anthers; on shorter stamens 7A, on longer stamens 182A, filaments; on shorter stamens NN155D, on longer stamens 63A, pollen; moderate in quantity and 20A in color.

*Pistils*.—1, an average of 2 cm in length, style; an average of 1.9 cm in length, color; base to center 180C, center to top 182A, stigma; rounded and flat in shape, N186A in color, 1 mm in diameter, ovary; superior, round, 19B in color and 5 mm in diameter.

*Fruit and seed*.—Fruit; circular in shape, 9 mm in length and diameter, immature 144C in color, mature base 144C, top 144A, surface is glossy and glabrous, flesh is 144A and 145C in color, seed; each capsule contains about 20 seeds an average of 2 mm in length width, deltoid in shape, and 144C in color.

It is claimed:

1. A new and distinct cultivar of *Lagerstroemia* plant named 'Baillagtwo' as herein illustrated and described.

* * * * *